US009645042B2

(12) United States Patent
Berchtold

(10) Patent No.: US 9,645,042 B2
(45) Date of Patent: May 9, 2017

(54) RESONANCE TESTING MACHINE

(71) Applicant: Russenberger Prüfmaschinen AG, Neuhausen am Rheinfall (CH)

(72) Inventor: Jürg Berchtold, Schaffhausen (CH)

(73) Assignee: RUSSENBERGER PRÜFMASCHINEN AG, Neuhausen am Rheinfall (CH)

( * ) Notice: Subject to any disclaimer, the term of this patent is extended or adjusted under 35 U.S.C. 154(b) by 216 days.

(21) Appl. No.: 14/660,311

(22) Filed: Mar. 17, 2015

(65) Prior Publication Data

US 2015/0268127 A1    Sep. 24, 2015

(30) Foreign Application Priority Data

Mar. 18, 2014  (EP) .................................... 14000991

(51) Int. Cl.
*G01N 3/32*  (2006.01)
*G01N 3/38*  (2006.01)
*G01M 7/02*  (2006.01)

(52) U.S. Cl.
CPC ............... *G01M 7/02* (2013.01); *G01N 3/32* (2013.01); *G01N 3/38* (2013.01); *G01N 2203/0073* (2013.01); *G01N 2203/0266* (2013.01)

(58) Field of Classification Search
CPC .... G01N 3/38; G01N 3/32; G01N 2203/0073; G01N 2203/0266; G01M 7/02
USPC ......................................................... 73/662
See application file for complete search history.

(56) References Cited

U.S. PATENT DOCUMENTS

| 2,890,584 | A | * | 6/1959 | Dickie | .................. | G01M 7/022 |
| | | | | | | 73/665 |
| 4,428,238 | A | * | 1/1984 | Tauscher | ................. | B06B 1/183 |
| | | | | | | 137/625.65 |
| 4,445,381 | A | | 5/1984 | Russenberger | | |
| 6,257,067 | B1 | * | 7/2001 | Ankrom | .................. | G01M 7/04 |
| | | | | | | 73/663 |
| 7,404,334 | B2 | * | 7/2008 | Saari | ........................ | G01N 3/02 |
| | | | | | | 73/760 |

(Continued)

FOREIGN PATENT DOCUMENTS

| CN | 2570766 | * | 9/2003 |
| DE | 3102778 | | 12/1981 |

(Continued)

OTHER PUBLICATIONS

European Search Report mailed Jun. 24, 2014 for European Application No. 14000991.1-1553.

*Primary Examiner* — J M Saint Surin
(74) *Attorney, Agent, or Firm* — RatnerPrestia

(57) ABSTRACT

Resonance test machine for vibration strength testing of a test body which is clamped between a cross member and a vibration head. The vibration head, test body and cross member are part of a second sub-oscillatory system which is vibratable in an axis x, in which the test body and a resonator containing the vibration head, a vibration spring and a vibration body are arranged successively in series along the x axis. A first sub-oscillatory system, which is also vibratable in axis x, is present in series to the second sub-oscillatory system and the resonator, wherein the first sub-oscillatory system contains the vibration body, spring elements, a seismic mass and electromagnetic vibration exciters.

18 Claims, 2 Drawing Sheets

(56) References Cited

U.S. PATENT DOCUMENTS

| | | | | |
|---|---|---|---|---|
| 7,540,195 B2* | 6/2009 | Nelsen | ................... | G01M 7/022 |
| | | | | 73/666 |
| 9,010,188 B2* | 4/2015 | Tustaniwskyj | ........ | G01M 7/022 |
| | | | | 73/662 |
| 2012/0306119 A1* | 12/2012 | Boes | ..................... | F16F 1/3842 |
| | | | | 264/250 |

FOREIGN PATENT DOCUMENTS

| DE | 4341127 | 6/1995 |
|---|---|---|
| DE | 10206710 | 8/2003 |

\* cited by examiner

RESONANCE TESTING MACHINE

CROSS-REFERENCE TO RELATED APPLICATIONS

This application claims priority to European Application No. 14000991.1, filed Mar. 18, 2014, the entire disclosure of which is incorporated herein by reference in its entirety for all purpose

FIELD OF THE INVENTION

The invention concerns a resonance testing machine for vibration strength testing of a test body clamped between a cross member and a vibration head, wherein the vibration head, the test body and the cross member are part of a second sub-oscillatory system which is vibratable in axis x, in which the test body and a resonator containing the vibration head, a vibration spring and a vibration body are arranged successively in series along axis x.

BACKGROUND OF THE RELATED ART

In material testing, tests with dynamic mechanical load changes on test bodies are widely known. For this, widely varying types of test machine are used with different working methods, wherein as well as mechanical systems, in particular three drive types are distinguished: namely hydraulic systems, ultrasound systems and electromagnetic systems.

Hydraulic systems achieve a working frequency, i.e. a load frequency to be transmitted to a specimen, of less than 1000 Hz and require a high energy input, since an oil pressure controlled with working frequency must move a working piston. Furthermore, hydraulic systems usually require multistage valve controls which often necessitate high maintenance costs.

Ultrasound systems, i.e. oscillatory systems with an ultrasound emitter, typically achieve 15,000 to 20,000 load changes per second. Thus systems excited with ultrasound indeed have a high working frequency, but these high frequencies lead to often unacceptable heating of the test specimen, whereby the material tests must usually be carried out intermittently, i.e. with interruptions for intermediate cooling for the test specimen. In such material testing, however, it is often unclear how the load changes should be evaluated at the start and end of an interval. Due to the cooling intervals, the duration of the material test—despite the high working frequency—is greatly increased. Furthermore, for physical reasons, not all specimen forms can be tested with this method. Also the material stress in the test body is measured indirectly.

Electromagnetic systems are generally operated in resonance and usually excited with one or more electromagnets with working frequencies (base frequency of natural vibration) of typically 30 to 250 Hz, i.e. load changes per second. Such systems work as mechanical resonators with electromagnetic excitation.

A mechanical resonance testing machine with electromagnetic excitation is described in DE A1 31 02 778. This resonance testing machine has a seismic mass, a frame established thereon with a horizontal cross member, a vibration body held sprung by means of a pretension spring from the cross member, and a vibration exciter held between the vibration body and the test body. The test body is arranged between the vibration body and the seismic mass. Furthermore, the resonance test machine has a central threaded spindle between the cross member and the pre-tension spring, in order to overlay a static stress over the vibration stress exerted on the test body during the vibration strength test. The vibration exciter is fitted with two parts which are moveable relative to each other for vibration excitation, and of which one is connected to the vibration body and the other to a holding element for the test body. The two vibration exciter parts are connected together by rod-like elastic elements, the length of which is dimensioned such that an air gap is present between the two vibration exciter parts under all conceivable operating conditions, allowing vibration excitation with good efficiency.

The resonance test machine according to DE A1 31 02 778 is also described as a three-mass resonance test machine containing the vibration body, the mass of the vibration exciter part connected to the holding element, and the seismic mass. The vibration body, the vibration exciter with the two vibration exciter parts and the elastic elements, the test body and the seismic mass, all lie in one axis, namely in a normal to the base surface. In this arrangement, the spring constant of the system determining the resonant frequency arises from the spring constants of the elastic elements of the vibration exciter and that of the test body. The spring constant f of a spring bar is generally proportional to the modulus of elasticity E of the spring bar, i.e. $f = E \cdot A/l_o$, wherein A is the cross sectional area of the spring bar and $l_o$ the mechanically unloaded length of the spring bar.

For the fatigue test of materials in industry and material research, today load change figures of the order of a few dozen (low cycle fatigue or LCF) up to multiples of $10^6$ (high cycle fatigue or HCF) are required. Sometimes even load change figures up to $10^9$ (very high cycle fatigue or VHCF) are required. In order to carry out material tests within an economically or technically acceptable test duration therefore the working frequencies must be increased. Previously known systems cannot, however, easily be adapted to modern requirements with regard to the significantly higher working frequencies.

SUMMARY OF THE INVENTION

An object of the present invention is to provide a compactly constructed resonance test machine, i.e. a test machine with an electromagnetically excitable resonator, for vibration strength testing of test bodies to be studied, the working frequencies of which in continuous use lie between 1000 and 2000 Hz.

To achieve this object, the preparation of a resonance test machine is proposed, wherein the resonance test machine is for vibration strength testing of a test body clamped between a cross member and a vibration head, wherein the vibration head, the test body and the cross member are part of a second sub-oscillatory system which is vibratable in axis x, in which the test body and a resonator containing the vibration head, a vibration spring and a vibration body are arranged successively in series along axis x, wherein a first sub-oscillatory system, which is also vibratable in axis x, is present in series to the second sub-oscillatory system and the resonator, wherein the first sub-oscillatory system contains the vibration body, spring elements, a seismic mass and electromagnetic vibration exciters.

Preferred embodiments are described in the dependent claims.

DETAILED DESCRIPTION OF CERTAIN EMBODIMENTS OF THE INVENTION

Figure 1:
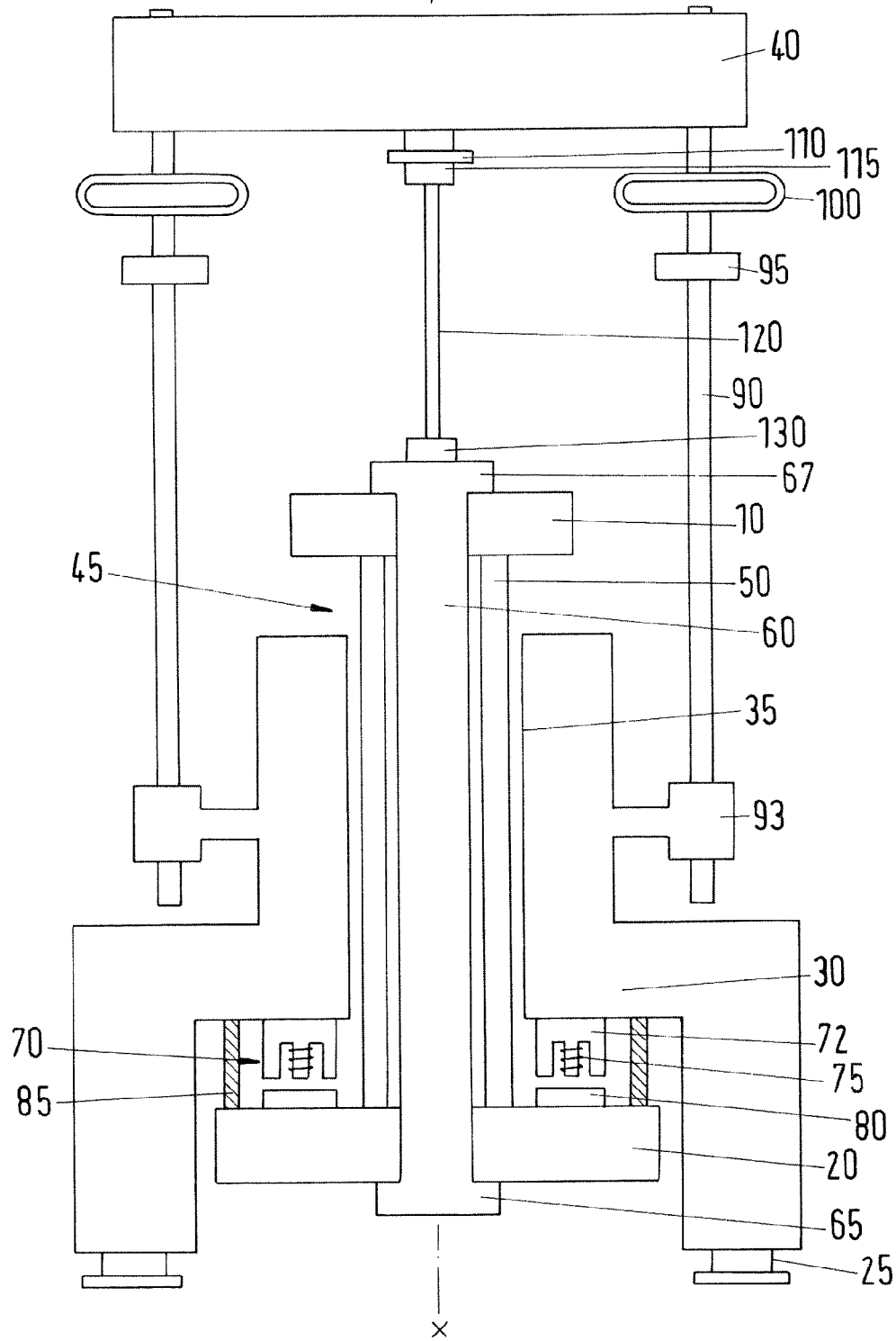
FIG. 1 is a schematic depiction of a longitudinal section through the longitudinal axis x of a resonance test machine according to the invention.

The resonance test machine according to the invention is a four-mass resonance test machine and contains in series three oscillatory systems coupled to each other with four participating masses, namely the seismic mass, the vibration body, the vibration head and the cross member. The seismic mass and the mass of the cross member are substantially larger than the masses of the vibration body and the vibration head. The term 'seismic mass' means a very large mass in comparison with the other masses participating in the oscillatory system.

The oscillatory systems which are present in series are firstly the resonator and secondly two sub-oscillatory systems, wherein the resonator is arranged between the two sub-oscillatory systems. The resonator is designed such that its natural frequency lies in the range between 1000 and 2000 Hz, particularly preferably in the range from 1000 to 1500 Hz. This resonator configuration is achieved by corresponding selection of the masses involved, namely the mass of the vibration body and the mass of the vibration head, and the design of the vibration spring lying between these masses, wherein the configuration concerns in particular the selection of the modulus of elasticity (known as the E modulus) and the dimensioning of the vibration spring.

The vibration head, the test body and the cross member are thus part of the second sub-oscillatory system which is vibratable in axis x, the oscillation frequency of which is determined by the resonator, wherein the resonator consists of the vibration head, the vibration spring and the vibration body. The vibration body is also called the counter-mass.

The first sub-oscillatory system is formed by the seismic mass, the vibration body and a number of spring elements lying in between, wherein at least one electromagnetic vibration exciter is present parallel to the spring elements. Each vibration exciter consists of two vibration exciter parts, namely an electromagnet containing a core with a coil and an anchor plate. The spring constants of the spring elements are selected such that an air gap of typically 0.1 to 0.5 mm exists between the anchor plate and the electromagnet in all proposed operating conditions.

The second sub-oscillatory system contains the masses of the vibration head and the cross member, while the test body which is clamped between the two said masses acts as a spring element.

The two sub-oscillatory systems and the resonator all lie in one axis, namely along axis x which typically lies perpendicular to the base surface on which the resonance test machine is erected.

The resonance test machine according to the invention therefore uses the swing head firstly as a mass of the resonator and secondly as a mass of the second sub-oscillatory system. Also, the vibration body is used firstly as a mass of the first sub-oscillatory system and secondly for the resonator.

The resonance test machine according to the invention serves for vibration strength testing of a test body which is clamped between a cross member and a vibration head of the test machine. The vibration body, test body and cross member form part of a second sub-oscillatory system which is vibratable in an axis x. The vibration head is excited by a resonator which is arranged in series to the second sub-oscillatory system along axis x. The resonator is configured to vibrate with a natural frequency between 1000 and 2000 Hz. The second sub-oscillatory system which is excited by the vibration head oscillates with a super-critical frequency, i.e. with a frequency higher than the natural frequency of the second sub-oscillatory system. The natural frequency of the second sub-oscillatory system typically lies between 300 and 600 Hz. The vibration head, however, vibrates with a frequency between 1000 and 2000 Hz.

The resonator is excited, i.e. set in harmonic oscillation, by the first sub-oscillatory system. The first oscillatory system also vibrates with a super-critical frequency, i.e. a frequency higher than the natural frequency of the first sub-oscillatory system. The natural frequency of the first sub-oscillatory system typically lies between 100 and 300 Hz. The first sub-oscillatory system consisting of the vibration body, seismic mass and spring elements is excited by one or more vibration exciters. Each vibration exciter here contains an anchor plate mechanically rigidly connected to the vibration body, and an electromagnet rigidly connected to the seismic mass. The electromagnet contains a core with an electrically conductive coil. The electromagnetic vibration exciters are always arranged parallel to the spring elements.

The vibration head is elastically coupled to the vibration body by way of the vibration spring such that the vibration head is set in a longitudinal harmonic oscillation along axis x under the effect of the first sub-oscillatory system.

Preferably, the resonator consisting of the vibration head, vibration spring and vibration body is mechanically connected to the seismic mass only by way of the spring elements of the first sub-oscillatory system.

The spring constants of the vibration spring and the spring elements are preferably each at least 5 times, preferably more than 10 times and up to 100 times, greater than the spring constant of the test body.

During a resonance test of the test body, the latter is usually under a static compressive or tensile stress i.e. the dynamic vibration stress on the test body is overlaid by a static compressive or tensile stress. For this, the cross member is preferably arranged moveably relative to the seismic mass. Since the spring constants of the vibration spring and the spring elements are preferably substantially greater than the spring constant of the test body, the distance between the cross member and the vibration head can be adjusted thanks to the movability of the cross member relative to the seismic mass.

The cross member is preferably connected to the seismic mass by way of at least one spindle column, wherein the length of each spindle column lying between the seismic mass and the cross member can be adjusted by means of a separate spindle drive. Here, however, synchronous activation of the spindle drives must be ensured.

Due to the very great mass of the cross member relative to the vibration head and vibration body, its vibration amplitude is very small. In order to minimise further the vibration transmission from the cross member to the spindle columns, and to guarantee an elastic, static pre-tension between the cross member and each spindle column, preferably a pre-tension spring is provided between the cross member and each spindle column.

To measure and control the static compressive or tensile stress on the test body, each spindle column is equipped with a static force meter.

To measure and control the dynamic stress on the test body, and to control the electromagnetic vibration exciter, at least one dynamic force meter is arranged between the test body and the cross member.

Preferably, the mass of the vibration head is between 2 and 5 times smaller than the mass of the vibration body. The mass of the seismic mass is preferably between 2 and 5 times greater than the mass of the vibration body, and the mass of the cross member is preferably between 1.5 and 3 times greater than the mass of the vibration head.

In a further preferred embodiment of the resonance test machine according to the invention, the vibration spring elastically connecting the vibration head and the vibration body consists of a tube spring and an anchor spring running concentrically through the cylindrical cavity of the tube spring, wherein particularly preferably the tube spring comes to lie between the vibration head and the vibration body, and the vibration body is elastically clamped to the vibration head by way of the anchor spring. In view of the higher mechanical stress on the resonator in a resonance frequency range between 1000 and 2000 Hz, the vibration spring must have a very high stiffness. The anchor spring is therefore preferably used for installation of the vibration spring because in order to clamp a tube spring with a high stiffness, i.e. with a high spring constant, between the vibration body and vibration head with sufficient mechanical stability, very high compressive or tensile loads are required for installation of the vibration spring.

The tube spring and where applicable also the anchor spring preferably consist of aluminium or a high-strength aluminium alloy. This allows the spring constants necessary for the vibration spring to be achieved.

In a preferred embodiment, the seismic mass has a continuous spring recess along axis x, in particular in the form of a bore, for passage of the vibration spring of the resonator. In order here to guarantee an even mechanical vibration excitation of the vibration body along axis x, suitably at least two parallel-arranged vibration exciters are used. These vibration exciters are preferably arranged spaced apart at equidistant central angles relative to axis x.

Because of the large mass of the cross member, the second sub-oscillatory system may also be regarded as connected in parallel with the oscillatory system consisting of the series-connected resonator and first sub-oscillatory system. It is evident from this that the spring constant of the test body has no substantial influence on the oscillatory system consisting of the series-connected resonator and the first sub-oscillatory system. Consequently, it is virtually only the spring constant of the vibration spring which determines the frequency, and the spring constant of the test body only has a negligible influence on the test frequency i.e. on the resonant frequency of the resonator. Consequently, the masses participating in the resonator, i.e. the mass of the vibration body and the mass of the test head, together with the spring constant of the vibration spring, must be selected such that a resonance frequency between 1000 and 2000 Hz can be achieved. The vibration path on the vibration head must be configured such that sufficient vibration force is generated on the test body. The vibration path is preferably between 0.15 and 0.3 mm in each direction about the resting mass, i.e. in total±0.15 to±0.3 mm. Preferably, the vibration path is±0.2 mm.

Figure 2:
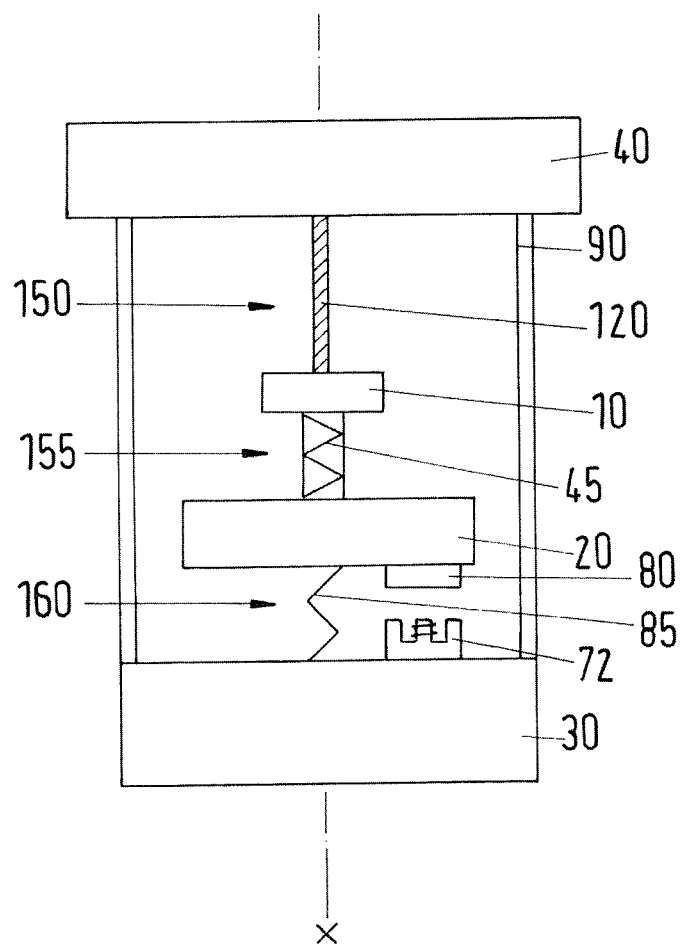
FIG. 2 is a diagrammatic depiction of the functional principle of the resonance test machine according to the invention.

Further advantages, features and details of the invention arise from the description below of preferred exemplary embodiments and the drawings which indicate diagrammatically:

FIG. 1 a schematic depiction of a longitudinal section through the longitudinal axis x of a resonance test machine according to the invention;

FIG. 2 a diagrammatic depiction of the functional principle of the resonance test machine according to the invention.

The longitudinal section through the resonance test machine according to the invention for vibration fatigue strength testing, shown diagrammatically in FIG. 1, has a seismic mass 30 fitted with elastic feet 25. At least two spindle drives 93 are fixedly connected to the seismic mass 30 and each hold a spindle column 90, wherein the spindle columns 90 are connected to a cross member 40 by way of a pre-tension spring 100. The cross member 40 is thus guided vertically moveably by the two spindle columns 90, wherein the spindle columns 90 and the two spindle drives 93 form an adjustment device for the cross member 40. In order to guarantee a synchronous movement of the cross member 40, the individual spindle drives 93 are preferably driven jointly by means of toothed belts (not shown) by way of one and the same motor-driven shaft (not shown).

The spindle columns 90 and spindle drives 93 allow adjustment of the distance between the cross member 40 and the seismic mass 30. Thus, a clamped test body 120 can be exposed to a static tensile or compressive load. The cross member 40 is connected to the seismic mass 30 by way of pre-tension springs 100. The pre-tension springs 100 transmit the static tensile or compressive load to the test body 120 and decouple the dynamic load from the seismic mass.

To measure the static compressive or tensile load on the test body 120, a static force meter 95 is fitted between the pre-tension springs 100 and the spindle columns 90.

A vibration body 20 is elastically connected to the seismic mass 30 by way of spring elements 85. Parallel to the spring elements 85, two electromagnetic vibration exciters 70 are situated between the vibration body 20 and the seismic mass 30. Each vibration exciter 70 has a first electromagnet 72 rigidly attached to the underside of the seismic mass 30 and made of ferromagnetic material, and provided with a magnetic core with an electrically conductive coil 75. Each vibration exciter 70 furthermore has a plate-like ferromagnetic anchor plate 80 which is moveable in the vertical axial direction x relative to the electromagnet 72 made of ferromagnetic material. The anchor plate 80 is rigidly connected to the vibration body 20. The two vibration exciter parts, namely the electromagnet 72 and the anchor plate 80, are bridged by the parallel-connected spring elements 85. At least one spring element 85 is assigned to each vibration exciter 70, and all spring elements 85 present are arranged concentrically about the longitudinal axis x. Preferably, two spring elements 85 are used per vibration exciter 70. The vibration exciters 70 with the assigned spring elements 85 are all constructed identically, and all spring elements 85 have the spring constant. The spring constant or spring stiffness of the spring elements 85 is dependent on their cross-sectional area and the modulus of elasticity of the spring material. The spring elements 85 are preferably made of sprung steel. Spring elements 85, together with the vibration body 20 and the seismic mass 30, form the first sub-oscillatory system 160 which is vibratable in the longitudinal axis x.

The spring elements 85 of the first sub-oscillatory system 160 are configured such that in each operating state of the resonance test machine, a clear space, i.e. an air gap, is present in the vibration exciter 70 between the electromagnet 70 and the anchor plate 80. A typical gap is between 0.1 and 0.5 mm.

The vibration body 20 has a circular cylindrical form for example. The vibration body 20 is connected centrally, i.e. axially to its longitudinal axis x, to a vibration head 10 by way of a vibration spring 45. The longitudinal axis of the vibration body 20, that of the seismic mass 30, the longitudinal axis of the vibration head 10 and that of the cross member firstly run parallel to the longitudinal axis of the resonance test machine and also coincide therewith. The vibration head 10 is preferably a circular cylindrical body. The vibration spring 45 shown in FIG. 1 consists of a tube spring 50 in the form of a hollow cylinder and an anchor spring 60 running inside the cylindrical cavity of the tube spring 50. The tube spring here consists of a metal tube, preferably an aluminium tube. The tube spring 50 is located between the vibration body 20 and the vibration head 10, wherein these three components are separably connected together, in particular screwed together, by means of the anchor spring 60. The anchor spring preferably takes the form of a metal bolt which has a thread at least in the two end regions, so that the three components, i.e. the vibration body 20, the vibration spring 20 and the vibration head 10, can be screwed together separably by means of a lower and an upper tie rod nut 65, 67. The metal bolt forming the anchor spring 60 preferably consists of aluminium. The anchor spring and the tube spring together form the vibration spring 45. The vibration body 20 and vibration head 10, screwed together and elastically connected by way of the vibration spring 45, form the resonator 155 which is mechanically connected to the seismic mass 30 only by way of the spring element 85, and to the cross member 40 by way of a test body 120 which may be clamped in the resonance test machine.

The longitudinal axis x of the resonator 155 coincides with the longitudinal axis x of the resonance test machine. The vibration spring 45 runs through a spring recess 35 in the seismic mass 30. The spring recess 35 of the seismic mass 30 runs continuously along axis x and preferably constitutes a longitudinal bore along axis x. Consequently, the seismic mass has a cylindrical recess 35 through which run the tube spring 50 and the anchor spring 60 of the resonator 155.

The resonator 155 is designed by its material selection and dimensioning such that it can vibrate only in the axial direction i.e. along axis x.

To undertake a vibration strength test on a test body 120, the test body 120 is clamped between an upper holding element 115 which is rigidly connected to the cross member 40 and a lower test body holding element 130 which is rigidly connected to the vibration head 10. The test body 120 together with the vibration head 10 and the cross member 40 thus forms the second sub-oscillatory system 150 which is vibratable in the longitudinal axis x.

Between the test body 120 or the upper test body holder 115 and the cross member 140 is a dynamic force meter 110, preferably a piezo element force meter, which can measure the dynamically acting forces of the vibrations.

The resonance test machine has an electronic unit (not shown). This contains firstly measurement and control electronics connected to the static force meter 95 and the gear motor for the spindle drive 93, and secondly measurement and control electronics connected to the dynamic force meter 110 and the vibration exciters 70. Furthermore, the control parts have adjustment functions in order to set certain parameters such as the amplitude of the vibration force or the static compressive or tensile force. On performance of a vibration strength test, the adjustment functions also serve to modify parameters according to a predefined programme.

When the test body 120 is subjected to a vibration strength test, vibration movements are generated running along the longitudinal axis x by means of the vibration exciters 70. As well as the test body 120, vibration head 10 and vibration body 20, further parts of the resonance test machine are brought to vibration, i.e. also the seismic mass 30 and the cross member 40 may be put into a slight oscillation, wherein, however, the corresponding vibration amplitudes are very small relative to the vibrations of the test body 120, the vibration head 10 and the vibration body 20 (because the masses of the seismic mass 30 and cross member 40 are much greater than those of the vibration body 20 and the vibration head 10).

FIG. 2 shows diagrammatically the functional principle of the resonance test machine according to the invention with the three series-connected oscillatory systems 150, 155, 160. Between the first and second sub-oscillatory systems 150, 160 is the resonator 155 containing the vibration head 10, vibration body 20 and vibration spring 45. The test body 120 is part of the second sub-oscillatory system 150 furthermore containing the vibration head 10 and the cross member 40. The first sub-oscillatory system 160 containing the vibration body 20, the seismic mass 30 and the spring element 85 serves for vibration excitation of the resonator 155, wherein the first sub-oscillatory system 160 can be excited by electromagnetic vibration exciters 70. For the sake of clarity, FIG. 2 does not show the means for static compressive or tensile loading of the test body 120.

What is claimed is:

1. A resonance test machine for vibration strength testing of a test body clamped between a cross member and a vibration head, wherein the vibration head, the test body and the cross member are part of a second sub-oscillatory system which is vibratable in axis x, in which the test body and a resonator, configured to vibrate with a natural frequency between 1000 and 2000 Hz, containing the vibration head, a vibration spring and a vibration body are arranged successively in series along axis x, wherein a first sub-oscillatory system, which is also vibratable in axis x, is present in series to the second sub-oscillatory system and the resonator, wherein the first sub-oscillatory system contains the vibration body, spring elements, a seismic mass and electromagnetic vibration exciters, wherein the vibration spring elastically connecting the vibration head and the vibration body consists of a tube spring and an anchor spring running concentrically through the cylindrical cavity of the tube spring, and wherein the tube spring comes to lie between the vibration head and the vibration body, and the vibration head is elastically clamped to the vibration body by way of the anchor spring.

2. A resonance test machine according to claim 1, wherein the vibration head is elastically coupled to the vibration body by way of the vibration springs such that the vibration head is configured to be brought into a longitudinal harmonic oscillation in axis x under the effect of the first sub-oscillatory system.

3. A resonance test machine according to claim 1, wherein the electromagnetic vibration exciters are arranged parallel to the spring elements.

4. A resonance test machine according to claim 1, wherein at least two parallel-arranged vibration exciters are present.

5. A resonance test machine according to claim 4, wherein the vibration exciters are arranged spaced at equidistant central angles relative to axis x.

6. A resonance test machine according to claim 1, wherein the spring constants of the vibration spring and spring elements are each at least 5 times greater than the spring constant of the test body.

7. A resonance test machine according to claim 1, wherein for static compressive or tensile loading of the test body, the cross member is arranged moveably relative to the seismic mass, and wherein the distance between the cross member and the vibration head is configured to be adjusted as a consequence of the series connection of the first and second sub-oscillatory systems and resonator.

8. A resonance test machine according to claim 7, wherein the cross member is connected to the seismic mass by way of at least one spindle column, and wherein the length of each spindle column lying between the seismic mass and the cross member is configured to be adjusted by means of a separate spindle drive.

9. A resonance test machine according to claim 7, wherein to decouple a vibration transmission from the cross member to the spindle columns, and to guarantee an elastic static pretension between the cross member and each spindle column, a pretension spring is present in each case.

10. A resonance test machine according to claim 9, wherein each spindle column is fitted with a static force meter to measure and control the static compressive or tensile stress on the test body.

11. A resonance test machine according to claim 1, wherein the resonator (155) comprising the vibration head, vibration spring and vibration body is mechanically connected to the seismic mass by way only of the spring elements of the first sub-oscillatory system.

12. A resonance test machine according to claim 1, wherein between the test body and cross member, a dynamic force meter is provided for measuring and controlling the dynamic load on the test body and to control the electromagnetic vibration exciter.

13. A resonance test machine according to claim 1, wherein the mass of the vibration head is between 2 and 5 times smaller than the mass of the vibration body.

14. A resonance test machine according to claim 1, wherein the mass of the seismic mass is between 2 and 5 times greater than the mass of the vibration body.

15. A resonance test machine according to claim 1, wherein the mass of the cross member is between 1.5 and 3 times greater than the mass of the vibration head.

16. A resonance test machine according to claim 1, wherein the tube spring and where applicable also the anchor spring is made of aluminium or a high strength aluminium alloy.

17. A resonance test machine according to claim 1, wherein the seismic mass has a continuous spring recess along axis x for passage of the vibration spring of the resonator.

18. A resonance test machine according to claim 17, wherein the continuous spring recess is in the form of a bore.

* * * * *